United States Patent
Sakaguchi

(10) Patent No.: US 8,509,511 B2
(45) Date of Patent: Aug. 13, 2013

(54) IMAGE PROCESSING APPARATUS AND X-RAY DIAGNOSTIC APPARATUS

(75) Inventor: Takuya Sakaguchi, Shioya-gun (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 1037 days.

(21) Appl. No.: 12/237,745

(22) Filed: Sep. 25, 2008

(65) Prior Publication Data

US 2009/0087068 A1    Apr. 2, 2009

(30) Foreign Application Priority Data

Sep. 28, 2007  (JP) ................ 2007-256337

(51) Int. Cl.
*G06K 9/00*    (2006.01)
(52) U.S. Cl.
USPC ......................................................... 382/131
(58) Field of Classification Search
None
See application file for complete search history.

(56) References Cited

U.S. PATENT DOCUMENTS

| | | | |
|---|---|---|---|
| 2007/0100223 A1* | 5/2007 | Liao et al. ................ | 600/407 |
| 2007/0232886 A1* | 10/2007 | Camus et al. ............. | 600/407 |
| 2009/0281418 A1* | 11/2009 | Ruijters et al. .......... | 600/424 |
| 2010/0061603 A1* | 3/2010 | Mielekamp et al. ...... | 382/128 |

FOREIGN PATENT DOCUMENTS

| | | |
|---|---|---|
| JP | 8-332191 | 12/1996 |
| JP | 2003-290192 | 10/2003 |
| JP | 2006-51359 | 2/2006 |
| JP | 2006-68350 | 3/2006 |
| JP | 2006-517822 | 8/2006 |
| JP | 2007-502646 | 2/2007 |
| JP | 2007-83048 | 4/2007 |
| WO | WO 2006/027781 A2 | 3/2006 |
| WO | WO 2006/066122 A2 | 6/2006 |

OTHER PUBLICATIONS

Office Action issued May 8, 2012, in Japanese patent Application No. 2007-256337 (with English-language translation).

\* cited by examiner

*Primary Examiner* — Brian P Werner
(74) *Attorney, Agent, or Firm* — Oblon, Spivak, McClelland, Maier & Neustadt, L.L.P.

(57) ABSTRACT

In an X-ray diagnostic apparatus, a volume 3D image in which a desired blood vessel center line has been extracted is stored in a CT 3D image storage unit, and an X-ray two-dimensional image updated in real time is stored in an X-ray 2D image storage unit. The three-dimensional image is aligned with the X-ray two-dimensional image in an alignment unit. Further, a distal end position of a device and a position thereof after a predetermined time are searched for in a search unit, and the distal end position of the device in the three-dimensional image is calculated in a computing unit. Then, a cross-sectional image of the three-dimensional image is displayed on a monitor.

12 Claims, 10 Drawing Sheets

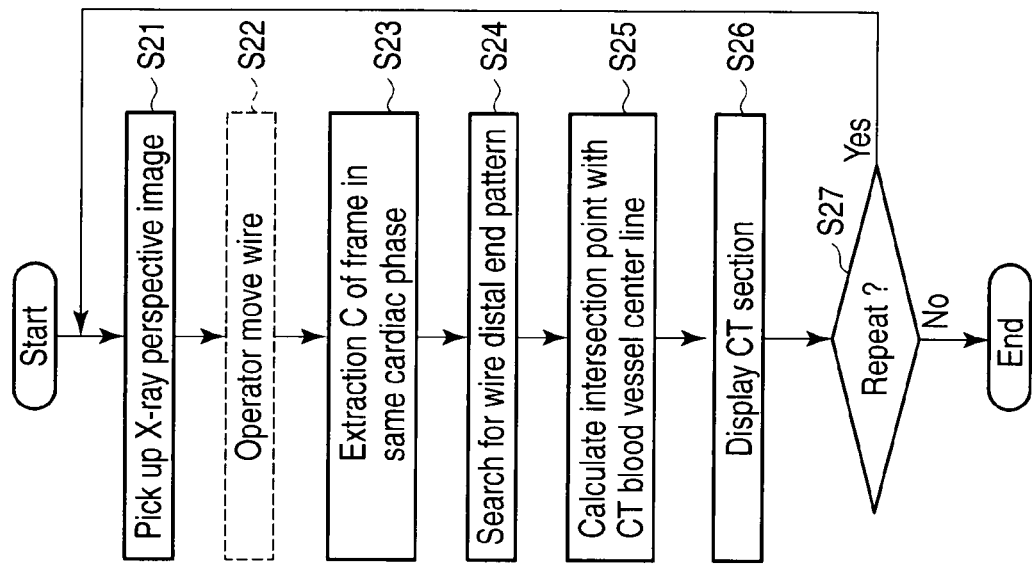
FIG. 5C
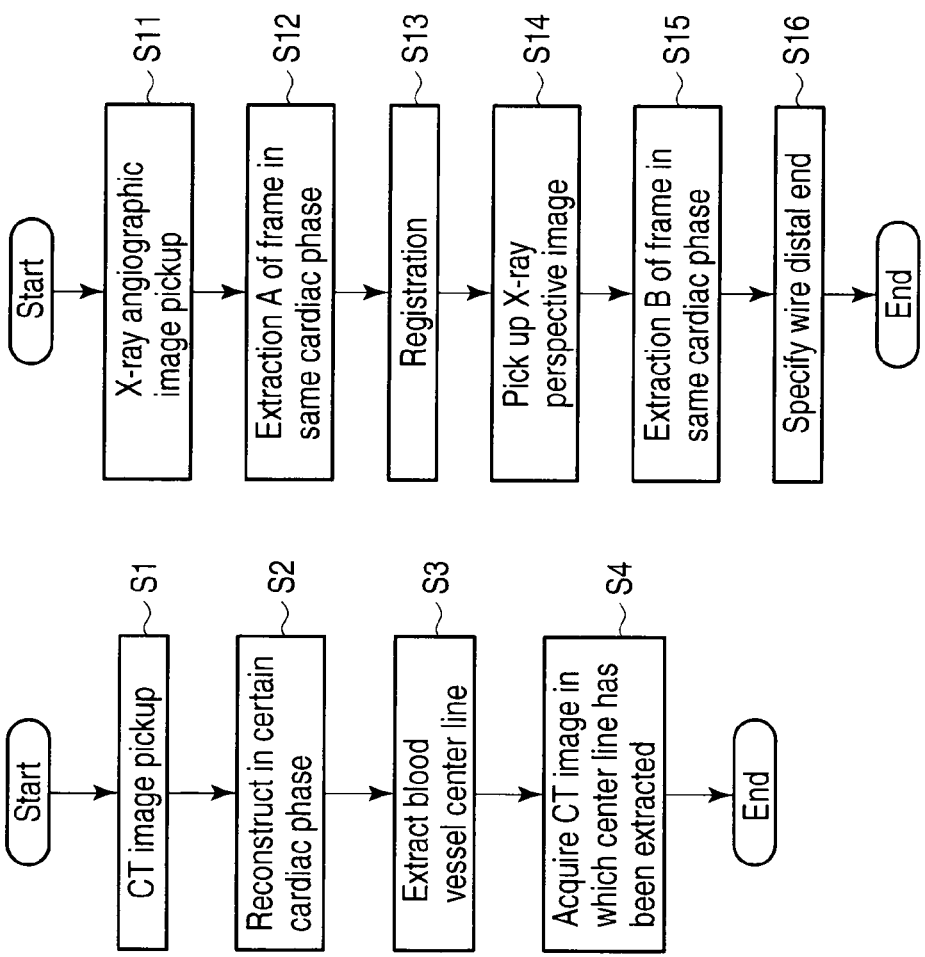
FIG. 5B
FIG. 5A

FIG. 6A
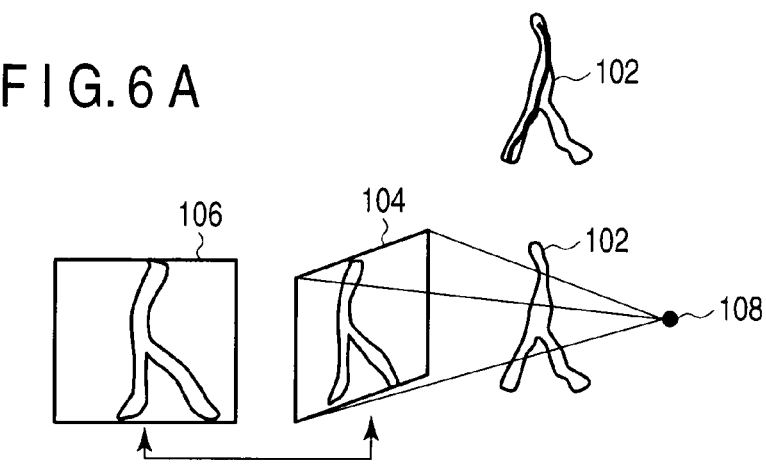
FIG. 6B
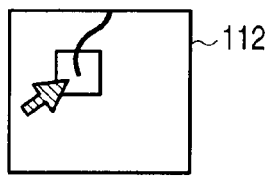
FIG. 6C
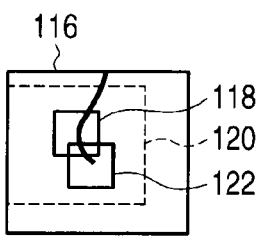
FIG. 6D
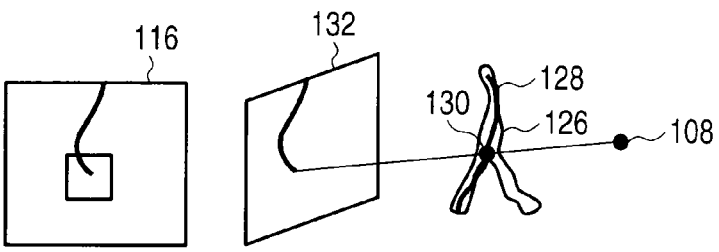
FIG. 6E
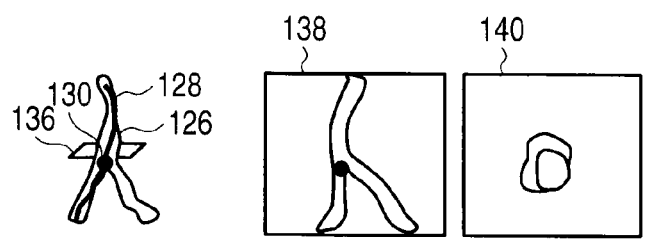
FIG. 6F ded in, for example, Jpn. Pat. Appln. KOKAI Publication No. 2003-290192. There have also been proposed various methods in the field of image processing.

IMAGE PROCESSING APPARATUS AND X-RAY DIAGNOSTIC APPARATUS

CROSS-REFERENCE TO RELATED APPLICATIONS

This application is based upon and claims the benefit of priority from prior Japanese Patent Application No. 2007-256337, filed Sep. 28, 2007, the entire contents of which are incorporated herein by reference.

BACKGROUND OF THE INVENTION

1. Field of the Invention

The present invention relates to an image processing apparatus and an X-ray diagnostic apparatus. More particularly, it relates to a support technique used in image pickup in an X-ray diagnostic apparatus whereby an operator moves a device into a blood vessel in an intravascular interventional treatment.

2. Description of the Related Art

Recent advances in CT imaging technology have made it easier to obtain a three-dimensional (3D) image of a cardiac coronary artery. Accordingly, there is an idea of using a CT 3D image to improve an intravascular treatment.

In an intravascular operation, an X-ray diagnostic apparatus is used, and a treatment is administered with a real-time view of its projection fluoroscopy image. Devices such as a catheter and a guide wire (hereinafter referred to as a wire) are used in the treatment. After the wire has been inserted into a coronary artery, it reaches a lesion through several vascular bifurcations, passes through the lesion, moves to a peripheral part with a small vessel diameter, and is fixed there. Once the wire is fixed, for example, a stenotic dilatation is administered using a device such as a stent. Then, the whole treatment operation is finished, and when it is judged in a final contrast study that the treatment can be ended, the wire which was first inserted and fixed is pulled out.

When the wire is first inserted, it is important to move the wire so that blood vessel walls may not be damaged. This must be taken care of particularly in the following cases: For example, as shown in FIG. 1A, a catheter 6 is inserted through a main artery 2, a coronary artery 4, etc., and force is applied at a part with a small thickness of the vessel wall so that a wire 8 may not break through the vessel. Otherwise, as shown in FIG. 1B, attention should be paid so that the wire 8 may not pick and break a soft tissue 10 such as soft plaque.

However, the X-ray fluoroscopy image does not enable the visualization of the thickness of the vessel wall and the softness of the plaque. Thus, at present, the wire is moved by the intuition and experience of an operator.

On the other hand, a recently available CT image has enabled the visualization of the thickness of the vessel wall and the softness of the plaque. There are therefore needs of operators that the CT image be utilized to display a cross-sectional image of the current position of the distal end of the wire being moved by the operator. That is, there is a desire that a cross-sectional image of a CT image corresponding to the distal end position of the wire being moved by the operator be displayed.

In order to achieve this, the following three steps are required: (i) adjustments of an X-ray two-dimensional (2D) image and a CT 3D image, (ii) the determination of three-dimensional coordinates of the distal end of the wire, and (iii) the determination of the direction of a section. Among these steps, (i) concerns the technical field called 2D/3D registration for aligning the 2D image with the 3D image, as As to (ii), it is theoretically impossible to obtain coordinates on the 3D image if coordinates on the 2D image in one direction of the X-rays are only obtained. While there have been various ideas to solve this, methods carried out with image processing have their limitations. Moreover, as to (ii), even if coordinates on the 2D image are obtained at a certain moment, the operator moves the wire at the next moment, thus coordinates on the 2D image are different at the next moment.

Therefore, it has been difficult in the prior arts to specify the coordinates of the distal end of the wire on the 3D image. Thus, for example, a technique using a three-dimensional position sensor has been proposed. However, this is a special tool and is not preferable.

Furthermore, (iii) can be theoretically achieved in image processing, but is difficult. That is, the travel of a blood vessel is determined from an image, and an image in a direction perpendicular to this travel is generated. This requires accurate binarization and extraction of the blood vessel, processing of branch vessels and analysis of the main components, therefore perfect determination of the travel is difficult in terms of image processing.

As described above, even if the prior arts are combined together, it has been difficult to display a cross-sectional image of a CT image corresponding to the distal end position of the wire being moved by the operator.

BRIEF SUMMARY OF THE INVENTION

It is therefore an object of the present invention to provide an image processing apparatus and an X-ray diagnostic apparatus capable of displaying a cross-sectional image of a CT image corresponding to the distal end position of a wire being moved by an operator and also displaying cross-sectional images in a moving manner to follow the movement of the wire by the operator.

Accordingly, the present invention is directed to provide an image processing apparatus comprising:

a first storage unit which previously stores a desired volume three-dimensional image;

a second storage unit which stores a sequentially updated two-dimensional image;

an alignment unit which aligns the three-dimensional image stored in the first storage unit with the two-dimensional image stored in the second storage unit;

a position acquisition unit which acquires a position of a device; and a computing unit which calculates the position of the device in the three-dimensional image.

The present invention is also directed to provide an X-ray diagnostic apparatus which displays an image by image processing of image data generated by detecting X-rays applied to a specimen and converting the X-rays to an electric signal, the X-ray diagnostic apparatus comprising:

a first storage unit which stores a desired volume three-dimensional image;

a second storage unit which stores a sequentially updated X-ray two-dimensional image;

an alignment unit which aligns the three-dimensional image stored in the first storage unit with the X-ray two-dimensional image stored in the second storage unit;

a position acquisition unit which acquires a position of a device; and a computing unit which calculates the distal end position of the device in the three-dimensional image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIGS. 5A, 5B and 5C are flowcharts for explaining the operation of the X-ray diagnostic apparatus according to one embodiment of the present invention;

FIGS. 6A to 6F are explanatory diagrams showing how to obtain a CT cross-sectional image in the X-ray diagnostic apparatus according to one embodiment of the present invention;

DETAILED DESCRIPTION OF THE INVENTION

Hereinafter, an embodiment of the present invention will be described with reference to the drawings.

Figure 1:
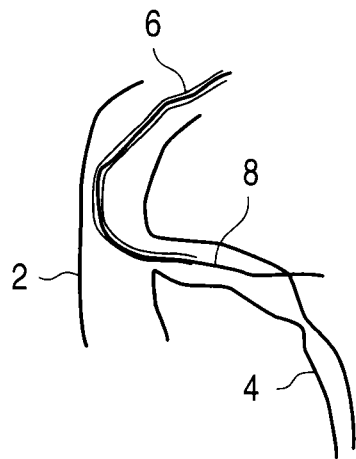
FIGS. 1A and 1B are diagrams showing examples of wire operation errors in a conventional intravascular treatment.
Figure 1:
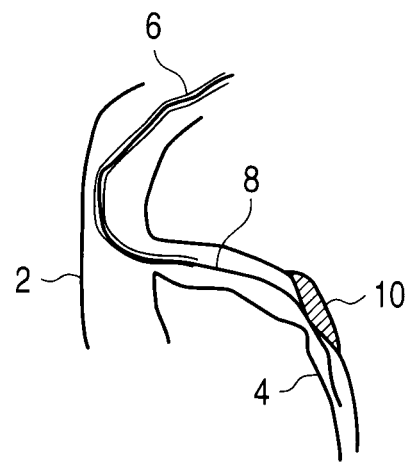
Figure 2:
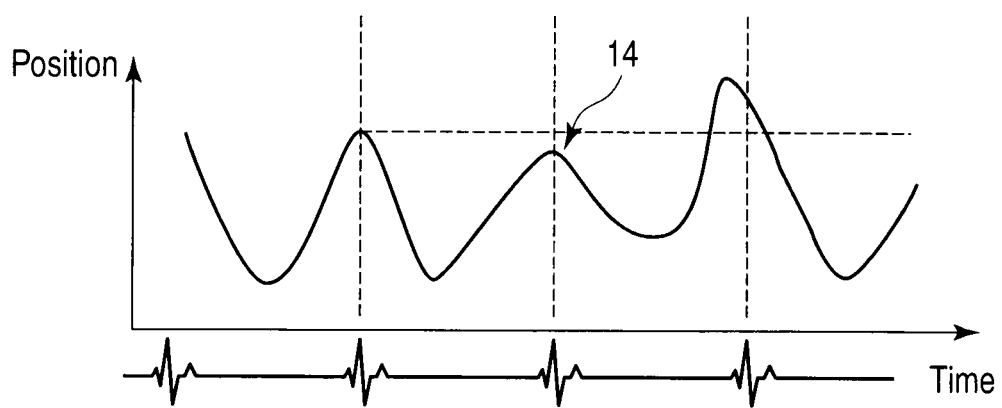
FIG. 2 is a diagram showing an example of a waveform of an electrocardiographic signal in a conventional X-ray diagnostic treatment.
Figure 3:
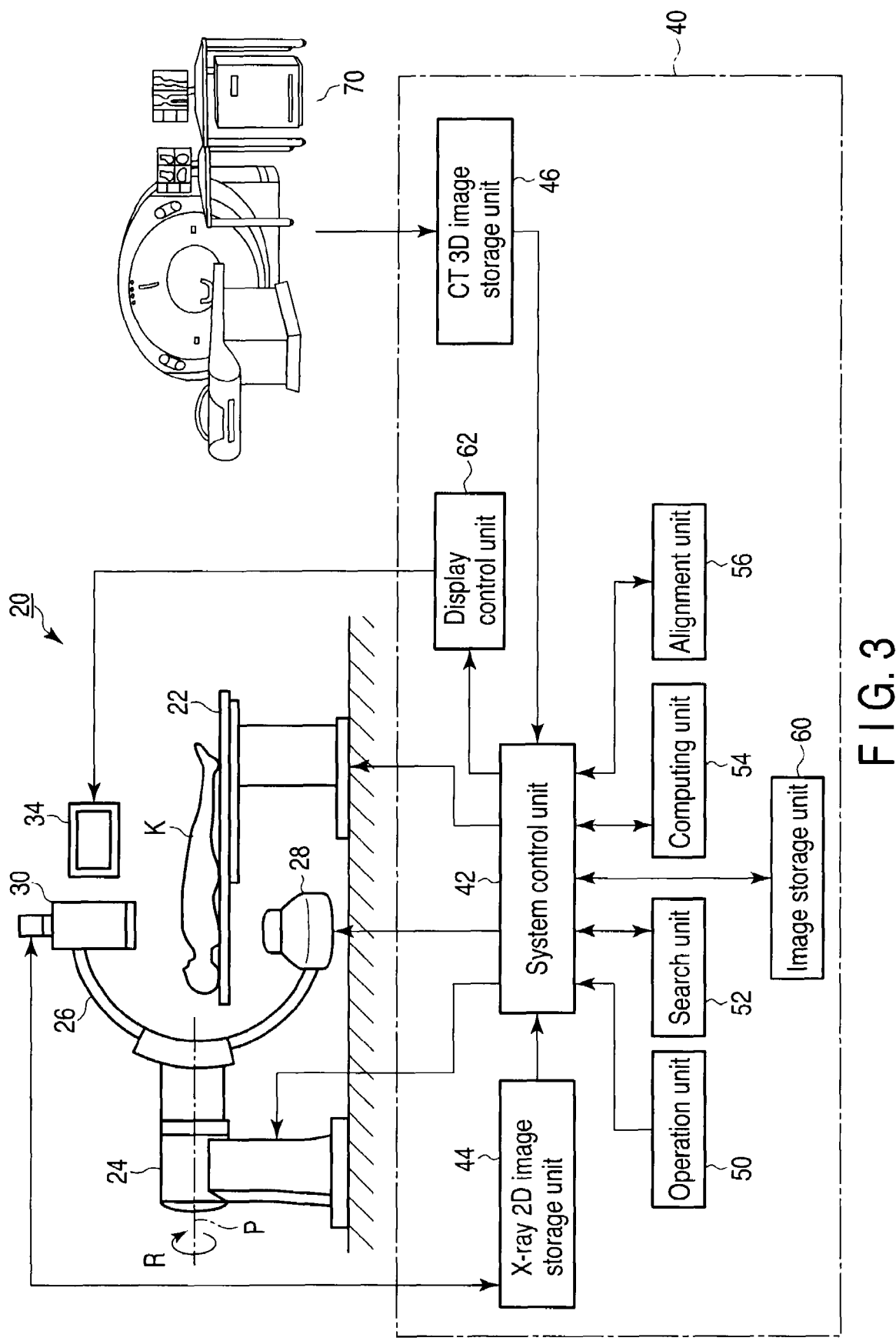
FIG. 3 is a block diagram showing the configuration of an X-ray diagnostic apparatus according to one embodiment of the present invention.

FIG. 3 is a block diagram showing the configuration of an X-ray diagnostic apparatus according to one embodiment of the present invention.

In FIG. 3, an X-ray diagnostic apparatus 20 comprises a bed 22 for mounting a patient (specimen) K, a stand 24, a C arm 26 which is supported on the stand 24 and which can turn in the direction of a shown arrow R around a shown P axis, an X-ray source 28 provided at one end of the C arm 26, an X-ray detector 30 provided at the other end of the C arm 26, a monitor 34 for displaying a generated image, and a controller 40 for controlling such equipment in cooperation.

The bed 22 is vertically and horizontally movable. Thus, the patient K is properly disposed between the X-ray source 28 and the X-ray detector 30.

The C arm 26 is configured to hold the X-ray source 28 and the X-ray detector 30 so that these are arranged opposite each other. Although not shown, the X-ray source 28 has an X-ray tube for applying X-rays to the patient K, and a collimator for collimating the X-rays emitted from the X-ray tube. On the other hand, the X-ray detector 30 is composed of, for example, an image intensifier (I.I.) and an optical system. The X-ray detector 30 converts X-ray information transmitted through the patient K by the I.I. into optical information, and collects the optical information in an optical lens by the optical system. In addition, an X-ray flat panel detector may be used as a detection unit instead of the I.I.

The controller 40 comprises a system control unit 42, an X-ray 2D image storage unit 44, a CT 3D image storage unit 46, an operation unit 50, a search unit 52, a computing unit 54, an alignment unit 56, an image storage unit 60, and a display control unit 62 for displaying a cross-sectional image of a 3D image on the monitor 34.

The system control unit 42 controls the positions of the bed 22 and the stand 24, controls the X-ray radiation in the X-ray source 28, and controls the X-ray detector 30. The X-ray 2D image storage unit 44 collects and stores X-ray 2D images. The CT 3D image storage unit 46 stores a volume 3D image in which a desired blood vessel center line has been extracted by a CT device 70.

The operation unit 50 selects a frame in a predetermined cardiac phase from the X-ray 2D image, and inputs the distal end position of an unshown device. The search unit 52 searches for a new distal end position of the device. The computing unit 54 calculates the position of the device in the 3D image. The alignment unit 56 aligns the 2D image with the 3D image. Further, the image storage unit 60 stores coordinates and images for the search for the position of the device. Moreover, the display control unit 62 displays the cross-sectional image of the 3D image on the monitor 34.

Figure 4A:
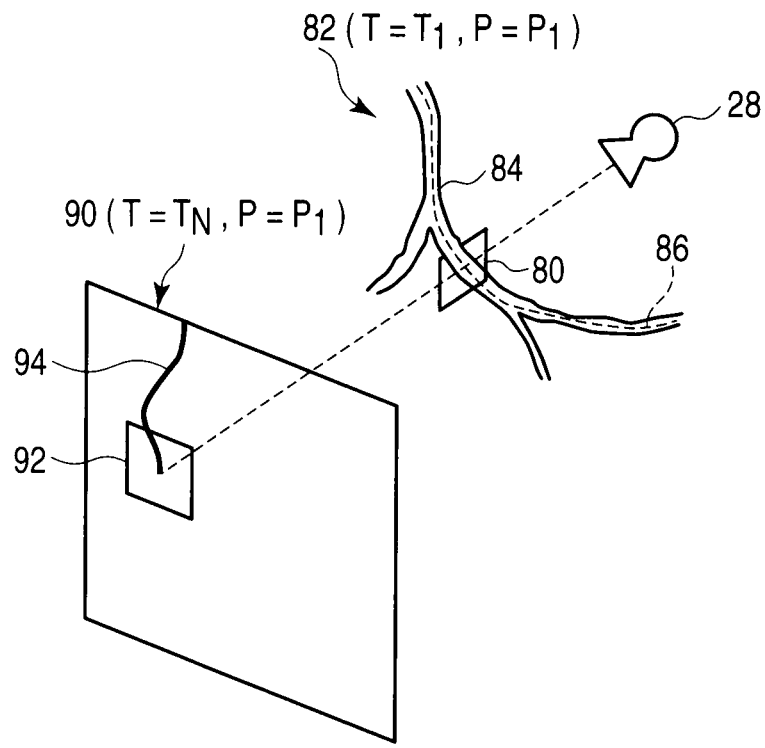
FIGS. 4A and 4B are diagrams for explaining the alignment of a three-dimensional image with a two-dimensional image.
Figure 4B:
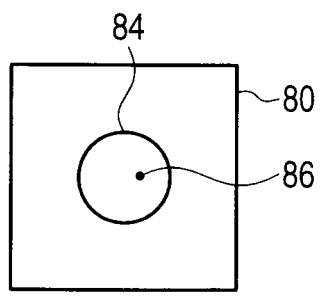

The X-ray diagnostic apparatus 20 having such a configuration is also adapted to the case where the operator moves a treatment device. This is achieved by calculating between a CT 3D image 82 and a 2D image (X-ray fluoroscopy image) 90 as shown in FIG. 4A. In the 2D image 90, an ROI image of the distal end position of a device such as a catheter 94 and its periphery is stored as a template 92. Additionally, a CT cross-sectional image 80 is displayed. This is achieved by cutting off and displaying a plane image perpendicularly intersecting with a center line 86 of an extracted CT vessel 84, as shown in FIG. 4B.

The operation in the present embodiment is described referring to flowcharts in FIGS. 5A, 5B and 5C.

In the case described here as an example, a CT image is provided as volume data, the distal end of a wire is provided as a device, a coronary artery of a heart is provided as a target organ, and an electrocardiographic signal is provided as a method of detecting heart movement.

First, operation as a past diagnosis is explained with the flowchart in FIG. 5A before the current diagnosis.

When the present routine is started, an image of the heart is picked up by the CT device 70 in step S1. Thus, the volume data for the heart is obtained. In the routine operation, this volume data is read by the operator. Then, when reconstruction is carried out in a certain phase in step S2, processing referred to as an analysis to extract a blood vessel center line is performed in subsequent step S3.

This analytic processing includes the operation of erasing unnecessary parts such as bones for a heart diagnosis, and the operation of solely extracting a blood vessel to be viewed. In the former, a mouse is clicked on a desired blood vessel. The blood vessel to be viewed may be finely extracted fully automatically. However, in many cases, the blood vessel to be viewed is input by clicking on a large number of points along the blood vessel to be viewed. The blood vessel to be viewed by the operator is, for example, an anterior descending branch (LAD), a circumflex branch (LCX) or a right coronary artery (RCA). In the present embodiment, a blood vessel having a lesion to be treated is defined as a blood vessel to be viewed.

X, Y, Z coordinate groups of the center line of the vessel to be viewed are obtained as data together with the volume data by the above analytic processing.

Then, in step S4, the obtained data is stored in the image storage unit 60 configured by, for example, a disk or a memory. Thus, as shown in FIG. 6A, a CT image (cardiac phase $P_1$) 102 in which the center line has been extracted is acquired.

The processing operations in steps S1 to S4 are all publicly known.

In addition, the data is not limited to the CT data, and MR volume data or angiography volume data is also applicable.

Next, the alignment operation of the X-ray diagnostic apparatus 20 in the present embodiment is described with reference to the flowchart in FIG. 5B.

When a patient to be treated actually enters/exits for a treatment by the X-ray diagnostic apparatus 20, the patient mounts the bed 22 to receive a treatment. Normally, contrast media is first injected into a blood vessel in step S11 so that an angiographic image is obtained. Normally, images are picked up from multiple directions so that multidirectional angiographic images are obtained. Then, in step S12, the cardiac phase (P1) is adjusted on the basis of the electrocardiographic signal between these 2D angiographic images and the CT 3D image which has been acquired in the above-mentioned flowchart in FIG. 5A, such that a frame is extracted.

Furthermore, alignment (registration) is carried out in step S13. Here, as shown in FIG. 6B, a CT projection image 104 from a virtual X-ray source 108 is aligned with an X-ray contrast image (cardiac phase $P_1$, time $T_1$) 106. For details of a method of an alignment technique, several methods have been known (e.g., several kinds of methods are described in detail in Jpn. Pat. Appln. KOKAI Publication No. 2003-290192 which is incorporated by reference herein). Paragraphs [0011]-[0013] and [0027]-[0035] of JP 2003-290192, a translation of which is provided below, with changes to the figure numbers, describe the alignment techniques.

To register both images, various methods are possible. In one method, at least one anatomical pixel or a plurality of markers can be identified in a two-dimensional (2D) perspective view, the same anatomical pixel or markers be identified in a three-dimensional (3D) reconstructed image, and the three-dimensional reconstructed image be aligned with the two-dimensional perspective image by parallel movement and/or rotation and/or two-dimensional projection with respect to the two-dimensional perspective image. As the anatomical pixel, a surface of the heart, for example, can be used. In this case, the three-dimensional reconstructed image is rotated or moved until its position coincides with the position of the two-dimensional perspective image, based on the identification of the anatomical pixel. In some cases, a so-called "figure-based" registration is performed using a method of performing changes in the projected image. So-called landmarks are used as the markers, and may be anatomical ones. As the landmarks, a particular blood vessel branch point, a small segment in the coronary artery, etc., can be exemplified. These can be interactively determined by a doctor in the two-dimensional perspective image, and then be searched for and identified in the three-dimensional reconstructed image, using an appropriate analyzing algorithm, thereby performing adjustment. As a non-anatomical landmark, another type of marker of an arbitrary property can be used, as far as it can be identified in the two-dimensional perspective image or the three-dimensional reconstructed image. Regarding whether parameters unique to a two-dimensional perspective image pickup device are known, when these parameters (the distance between a focus and a detector, the pixel size of a detector element, the through-pass point of the detector at which the center light of an x-ray tube passes) are known, it is sufficient if at least four landmarks are identified. In contrast, if these parameters are unknown, at least six markers must be identified in each image.

In another method for registration, the use of two two-dimensional perspective images with a certain angle, preferably, 90 degrees defined therebetween is planned. In these images, a plurality of corresponding markers are identified, their three-dimensional volume positions are determined by back projection, and based on the determination result, a three-dimensional reconstructed image including corresponding identified markers is aligned by parallel movement and/or rotation and/or two-dimensional projection associated with the three-dimensional positions of the markers. In this case, 3D/3D registration is performed based on the markers' volume positions, unlike the above-described 2D/3D registration. The volume positions are determined from the intersections of back projection straight lines that extend from the respective markers to the X-ray tube focus.

There is yet another method, which is so-called "image-based" registration. In this method, one two-dimensional projected image is generated in the form of a digitally reconstructed radiogram (DRR) from a three-dimensional reconstructed image, and is compared with a two-dimensional perspective image in the degree of coincidence. To optimize the degree of coincidence, the two-dimensional projected image is moved by parallel movement and/or rotation in association with the two-dimensional perspective image until the degree of coincidence reaches a predetermined lowest value. At this time, it is advantageous to guide the generated two-dimensional projected image to a user, where the projected image is sent to a position as similar to the two-dimensional perspective image as possible, and then to start an optimization cycle to shorten the time required for calculation for registration. Instead of rough positioning of guiding the projected image to the user, it is possible to detect, for example, a position-associated imaging parameter, such as orientation via a C-arm position and its appropriate imaging means. This is because these elements are criteria associated with the position of the two-dimensional perspective image. Depending upon these information items, rough positioning can be performed using a computer. Whenever the degree of coincidence is calculated, and it is determined that the predetermined lowest value is not reached, a parameter for a transform matrix used to transform the two-dimensional projected image into a two-dimensional perspective image is newly calculated in order to increase the degree of coincidence, thereby modifying the degree of coincidence. The determination of the degree of coincidence can be performed based on, for example, each local gray value distribution. Alternatively, it is possible to evaluate a possible coincidence degree through an appropriate calculation algorithm.

Figure 13:
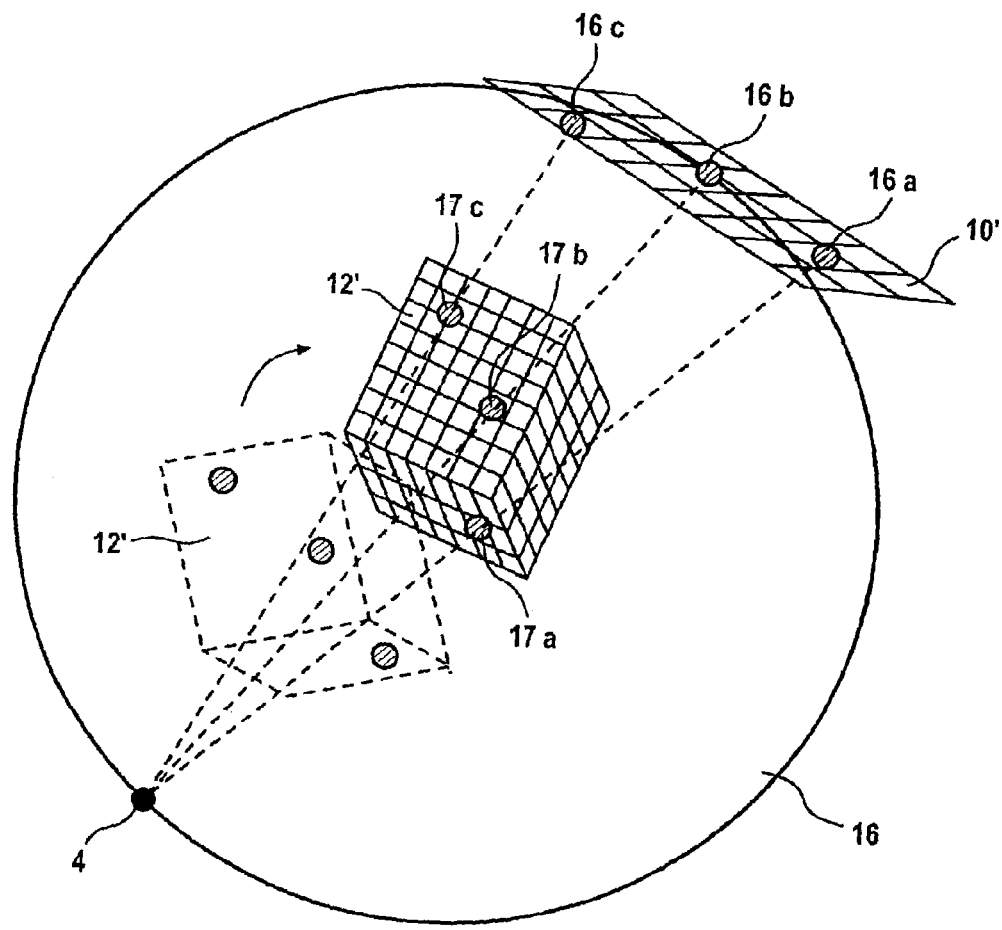
FIG. 13 shows a schematic sketch which explains the conventional registration of the 3d reconstructed image relative to a 2d x-ray image.

FIG. 13 shows a possibility of registering a three-dimensional reconstructed image and a two-dimensional perspective image on each other. More specifically, FIG. 13 shows a two-dimensional reconstructed image 10' detected by a detector 5 located at the same position, not shown. Further, it shows a locus 16 which includes the focus of a radiation source 4 and its vicinity, and along which the detector and a ray source are moved by a C-arm 3.

FIG. 13 also shows a currently-reconstructed three-dimensional image 12' that is not registered on the two-dimensional perspective image 10'.

To perform registration, in the two-dimensional perspective image 10', a plurality of markers (in the figure, three markers) or landmarks 16a, 16b and 16c are identified or defined. As the landmarks, a particular blood vessel branch point, a small segment in the coronary artery, etc., can be used. These landmarks can also be identified in a three-dimensional reconstructed image 12'. It is apparent that landmarks 17a, 17b and 17c are not positioned on the projected light beams passing from the radiation source 4 to the landmarks 16a, 16b and 16c of the two-dimensional perspective view 10'. If the landmarks 17a, 17b and 17c are projected on the detection surface, they apparently exist at positions different from those of the landmarks 16a, 16b and 16c.

To perform registration, the three-dimensional reconstructed image 12' is moved by parallel movement or rotation with strict registration until the landmarks 17a, 17b and 17c are projected on the landmarks 16a, 16b and 16c. In the shown case, the alignment of the registered three-dimensional reconstructed image 12' is drawn simply by, for example, the continuous lines of the reconstructed image shown as a cubic.

Figure 14:
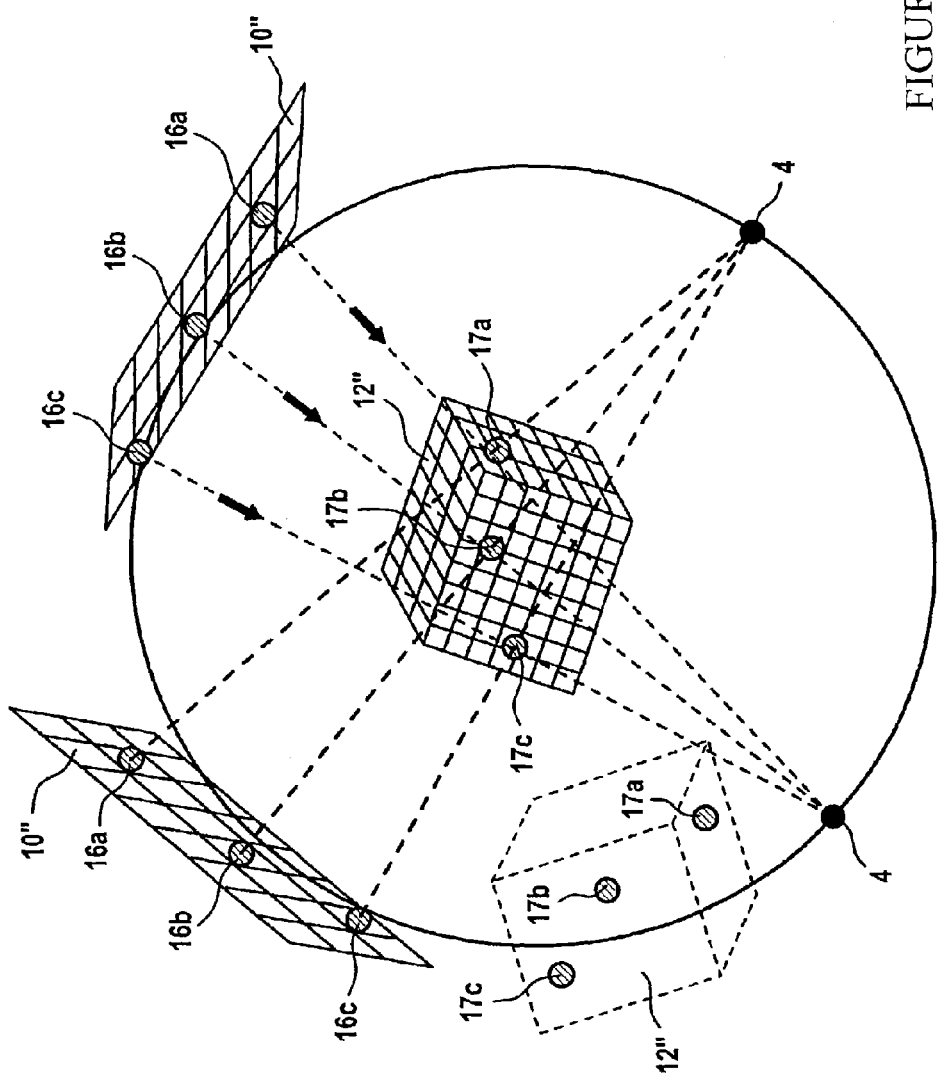
FIG. 14 shows a schematic sketch which explains the conventional registration of the 3d reconstructed image relative to two 2d x-ray images.

FIG. 14 shows a further possible method for registration. In this case, two two-dimensional perspective images 10" generated by imaging at two different radiation source detector positions are used. Preferably, these images are orthogonal to each other. The different positions of the radiation source 4 are shown, and from these positions, different positions of the radiation detector result.

At this time, the landmarks 16a, 16b and 16c are identified in the two-dimensional perspective image. Similarly, the corresponding landmarks 17a, 17b and 17c are identified in the three-dimensional reconstructed image 12". For registration, the three-dimensional volume positions of the landmarks 16a, 16b and 16c are determined. In an ideal case, these volume positions are set at the intersections of projected light beams passing from the landmarks 16a, 16b and 16c to the focus of the radiation source 4. The volume positions of the landmarks 16a, 16b and 16c around the isocenter of the C-arm as shown.

If the lines do not accurately intersect, the volume positions can be determined by appropriate approximate possibility. For instance, each volume position can be determined as a position at which two ideally intersecting lines exist with a minimum interval interposed therebetween.

For registration, also in this case, the three-dimensional reconstructed image 12" is moved by parallel movement or rotation, or two-dimensional projection (and further, expansion/contraction in size) depending upon the case, until the landmarks 17a, 17b and 17c exactly coincide with the volume positions of the landmarks 16a, 16b and 16c. The alignment at this time is also indicated by the continuous lines of the three-dimensional reconstructed image 12".

Figure 12:
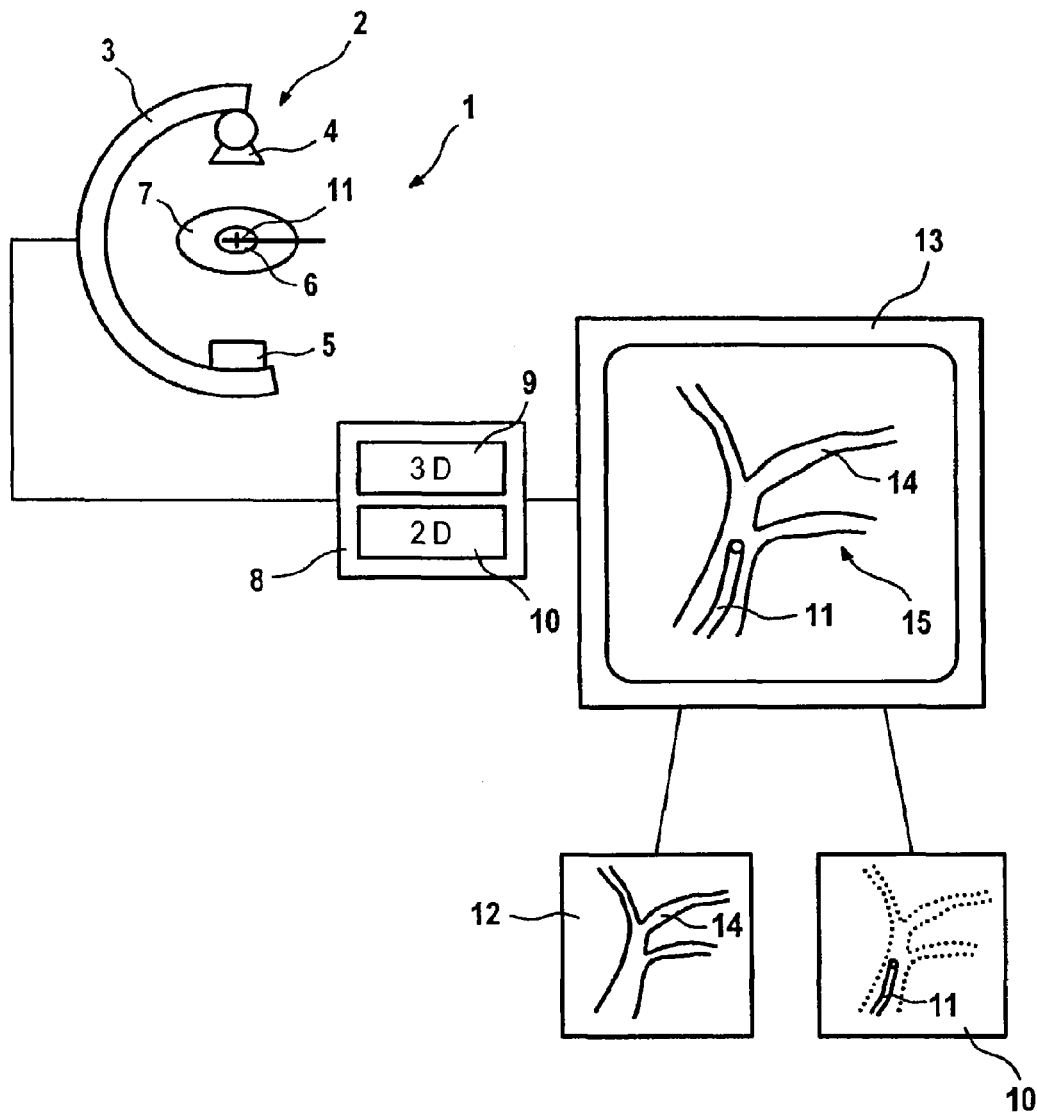
FIG. 12 shows a conventional schematic sketch of a medical examination and/or treatment device.

In accordance with the executed registration, accurate alignment can be realized as described in association with FIG. 12, regardless of the type of registration.

A patient to be treated actually mounts the bed for a diagnosis by the X-ray diagnostic apparatus, and receives a treatment. That is, an X-ray fluoroscopy image (a moving image, real time) is obtained as real-time imaging in step S14. While the above-mentioned imaging is carried out from multiple directions, an imaging direction is rarely changed in a fluoroscopy image pickup in a treatment after a direction in which an affected part is well viewed has been determined.

Then, in step S15, a desired frame is selected from the X-ray 2D image by the operation unit 50. The X-ray 2D image is a moving image whether it is a picked-up image or a fluoroscopy image, and is composed of 10 to 200 frames. In general, it is picked up at 10 to 30 frames/sec. Among these frames, a frame in the same cardiac phase $P_1$ as the cardiac phase in which CT has been reconstructed is extracted.

The cardiac phase is heartbeat movement, and is generally expressed in such a manner that an R wave is 0, the next R wave is 100, and the part therebetween is divided into 100 equal parts. Since the electrocardiographic signal is generally collected simultaneously with the collection of the X-ray 2D image, the electrocardiographic signal is monitored such that a frame imaged in the same cardiac phase as the CT alone is extracted in real time.

In addition, while the technique using the electrocardiographic signal is shown here, a technique which manually judges the cardiac phase by a method other than the electrocardiographic signal may be employed. For example, a technique which shows the movement of the wire in an image may be used.

Then, when frames in the same cardiac phase are obtained out of the fluoroscopy image, the first one is displayed in the screen of the monitor 34. Further, in step S16, the distal end of the wire is clicked by the operator with, for example, the mouse in the operation unit 50 through an interface. Thus, as shown in FIG. 6C, coordinates $(U_2, V_2 | P=P_1, T=T_2)$ of the wire distal end on the 2D image in the cardiac phase $P_1$ at time $T_2$ are obtained.

In addition, the method of specifying the wire distal end may be automated without depending on the manual input by the operator. In this case, a pattern of the distal end of the wire is provided as a template, and one similar to this template is searched for in the 2D image.

When the coordinates $(U_2, V_2 | P=P_1, T=T_2)$ of the distal end position of the device have been obtained, the coordinates and an image of a peripheral ROI are saved as a template in the image storage unit 60.

Then, in step S24, when the cardiac phase $P_1$ appears in the 2D fluoroscopy image being collected, a place similar to the previously saved template is searched for in this frame image. Here, the search may be made using a common method that searches for a place having the maximum similarity, and, for example, a technique that maximizes a cross-correlation value is employed. Thus, a new wire distal end position on the perspective 2D image $(U_3, V_3 | P=P_1, T=T_3)$ can be obtained.

As shown in FIG. 6D, coordinates $(U_2, V_2 | P=P_1, T=T_2)$ 118 of the wire distal end position obtained in the cardiac phase $P_1$ at the time $T_2$ are substantially located in the vicinity of the coordinates $(U_3, V_3 | P=P_1, T=T_2)$ in an image 116 in the cardiac phase $P_1$ at the time $T_3$. Small differences are made in a component attributed to the aperiodicity of the heart movement and in a component attributed to the movement of the wire by the operator. The former corresponds to about 5 mm at the maximum, and the latter corresponds to the distance in which the operator moves the wire during one heartbeat, that is, about 0.5 to 1 second, and is considered to be within about 10 mm at the maximum. Therefore, the movement is about 15 mm at the maximum, and a new wire distal end position can be found by searching a corresponding range 120. It is considered that there is little change in the shape of the wire during about 0.5 to 1 second, so that the new wire distal end position can be found.

In addition, when new coordinates have been obtained, the new coordinates $(U_3, V_3|P=P_1, T=T_3)$ 122 are saved, and an updated template is also saved.

At the next time $T_4$, the pattern at the $T_3$ is matched with a pattern at the $T_4$.

Figure 7:
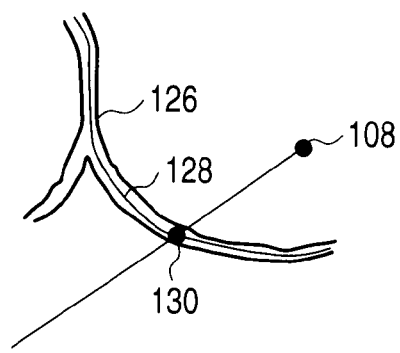
FIG. 7 is another explanatory diagram showing how to obtain a CT cross-sectional image in the X-ray diagnostic apparatus according to one embodiment of the present invention.

Moreover, while the distal end position of the wire (device) is obtained in the example described above, this is not a restriction. For example, as shown in FIG. 7, the position of a part of the wire may be detected and obtained.

FIG. 5C is a flowchart for explaining the operation of repetitive acquisition of X-ray fluoroscopy images in the X-ray diagnostic apparatus 20 in the present embodiment.

In step S16 in the flowchart in FIG. 5B, the X-ray fluoroscopy images are continuously collected even after the wire distal end has been specified. Therefore, if a repeat is to be made in step S27 described later, an X-ray fluoroscopy image is acquired in step S21 as in step S14 in the flowchart in FIG. 5B. After the wire has been moved to a new position by the operator in subsequent step S22, a frame in the same cardiac phase $P_1$ as the cardiac phase in which CT has been reconstructed is extracted in step S23 as in step S15 in the flowchart in FIG. 5B.

Since the 2D X-ray images have already been aligned with the CT 3D image in step S13 in the above-mentioned flowchart in FIG. 5B, the positional relation therebetween is known. Thus, in step S25, a straight line connecting the wire distal end position $(U, V|P=P_1, T=T_3)$ in the 2D image 116 with the X-ray source 108 is assumed, and an intersection point 130 of this straight line and the extracted CT center line is determined to be the distal end position $(X, Y, Z|P=P_1, T=T_3)$ of the device in the 3D image.

In addition, it is anticipated that they may not intersect completely at one point due to various error factors, in which case a point which minimizes the distance between a projector and the center line is substituted for. This is based on the assumption that the wire always passes through the blood vessel and that the wire always passes through the extracted blood vessel to be viewed.

When a blood vessel is not extracted in the CT image, an intersection point is not specified because there are a large number of intersection points of the projector and the blood vessels. As shown in FIG. 6E, a blood vessel center line 128 in a blood vessel 126 in the CT image has been extracted, so that an intersection point 130 of the projector from the X-ray source 108 and the blood vessel center line 128 can be found.

By the processing so far, the three-dimensional coordinates $(X, Y, Z|P=P_1, T=T_3)$ of the wire distal end position have been calculated. Therefore, the wire distal end position can be displayed as a point in the CT 3D image.

By the processing up to step S25, the three-dimensional coordinates $(X, Y, Z|P=P_1, T=T_3)$ of the wire distal end position have been calculated. Thus, in step S26, as shown in FIG. 6F, a plane 136 perpendicular to the extracted blood vessel center line 128 at a place where the CT extracted blood vessel center line 128 passes through the point (intersection point) 130 is cut out and serves as a vessel cross-sectional image 140. In addition, 138 denotes a CT image in the cardiac phase $P_1$.

In addition, while the vessel cross-sectional image is simply used in the present embodiment, any processed cross-sectional image may be used, such as a cross-sectional image divided by CT values or a cross-sectional image representing the hardness of a plaque.

Then, in step S27, whether to repetitively collect images is judged. The X-ray fluoroscopy images are continuously collected, so that a fluoroscopy image in the same cardiac phase as the CT image is obtained one time at one heartbeat. The above-mentioned processing operations are performed in each case. Thus, three-dimensional coordinates of the wire distal end are calculated one time at one heartbeat, and the cross-sectional image is updated one time at one heartbeat. That is, the processing operations in steps S21 to S27 are repeated substantially in real time.

When the collection of the fluoroscopy images is stopped, a wire distal end position $U_i, V_i$ in the final image in the same cardiac phase is stored. When the collection of the fluoroscopy images from the same angle is then resumed, a pattern in the vicinity of $U_i, V_i$ is searched for without manual operation. Thus, the image is updated with no need for manual specification as long as the angle of the C arm is not changed or the bed is not moved.

On the contrary, the system always monitors the angle of the C arm 26 and the movement of the bed 22. If a movement is detected, the updating of the cross-sectional image display is stopped, and the operator is requested to again input the distal end position of the wire.

Figure 8:
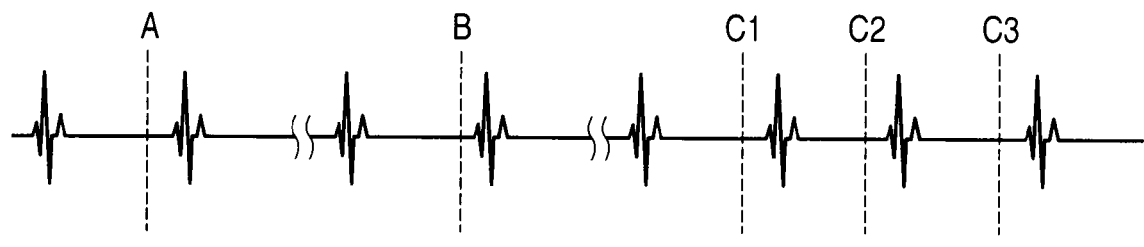
FIG. 8 is a diagram showing one example of a waveform chart of an electrocardiographic signal detected by the processing operations in accordance with the flowcharts in FIGS. 5A, 5B and 5C.

FIG. 8 shows one example of a waveform chart of an electrocardiographic signal detected by the above-mentioned processing operations in accordance with the flowcharts in FIGS. 5A, 5B and 5C. In addition, A, B indicated in the diagram represent the times of the processing operations in steps S12, S15 in the flowchart in FIG. 5B, and C1, C2, C3 represent the frames in the first, second and third processing operations in step S23 in the repeated flowchart in FIG. 5C.

Figure 9:
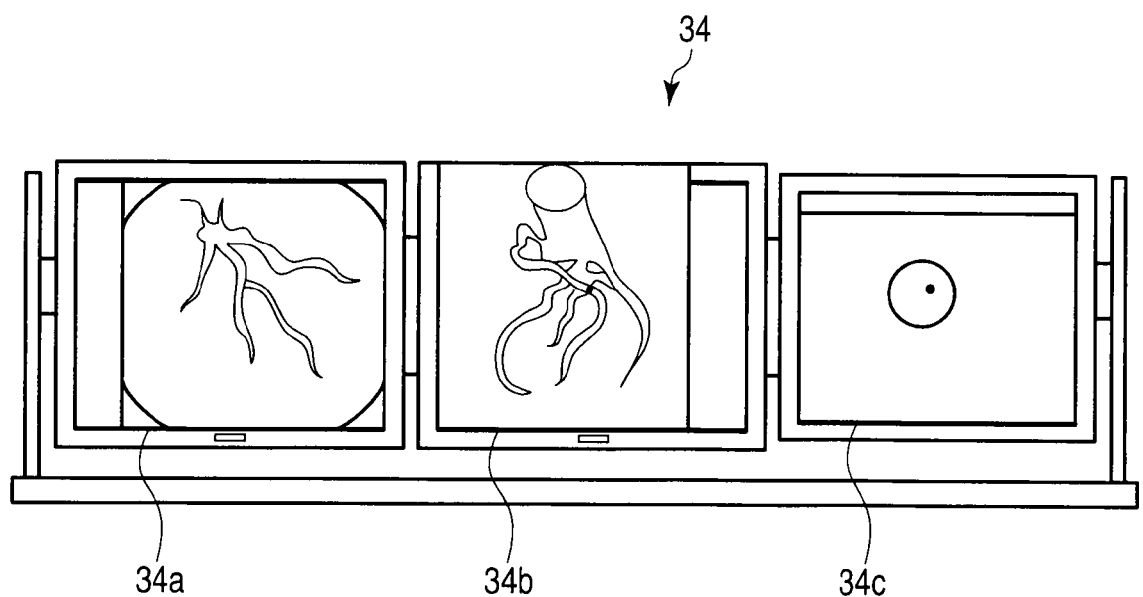
FIG. 9 is a diagram showing an example of display on a monitor 34.

As an example of display on the monitor 34, a three-screen configuration is preferable, for example, as shown in FIG. 9. Among these images, an X-ray fluoroscopy image 34a is updated, for example, every 33 msec. Further, a CT image 34b is not updated, but the position of a mark indicating the 3D coordinates of the wire distal end is updated one time at one heartbeat. Moreover, a CT cross-sectional image 34c is updated one time at one heartbeat.

Next, a modification of the above-mentioned one embodiment is described.

In the case described here, a blood vessel is bent, and two or more intersection points are calculated.

In the embodiment previously described, the projector and the center line of the blood vessel intersect at one place. However, when the blood vessel is extremely bent or bent in a depth direction (foreshortening), they do not always intersect at one place. In such a case, the movement of the wire does not suddenly leap and is continuous along the blood vessel, which results in the following consideration.

Figure 10:
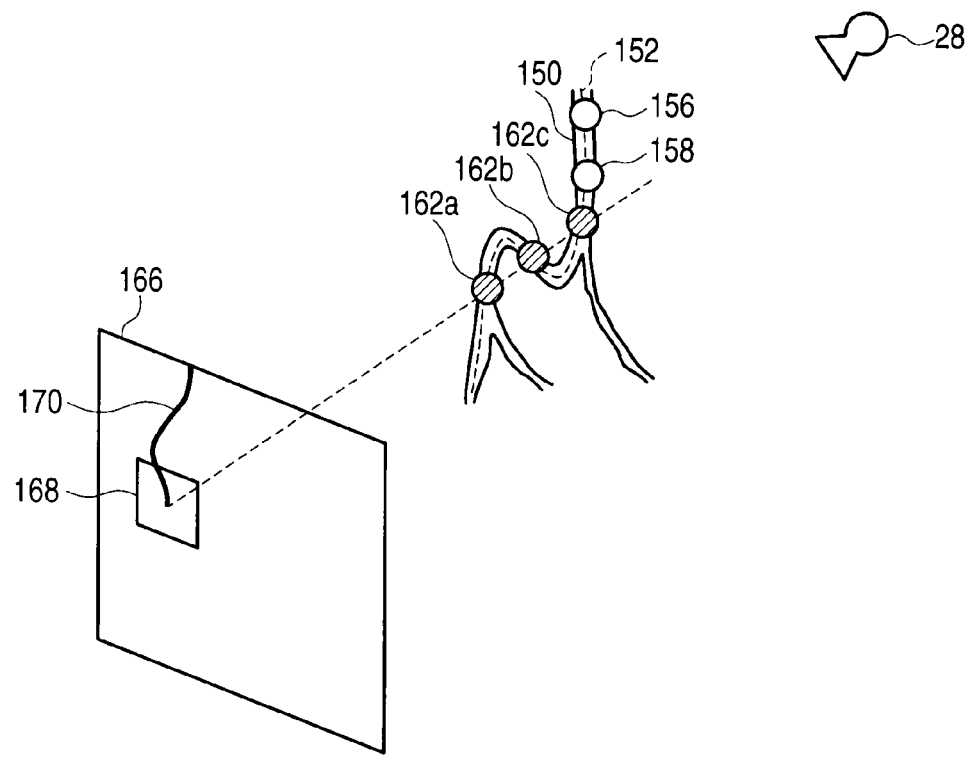
FIG. 10 is a diagram for explaining a modification of one embodiment of the present invention.

In FIG. 10, candidate points proximate to coordinates X, Y, Z of a candidate point 158 detected one point earlier among a plurality of candidate intersection points, for example, intersection points 156, 158 present are determined to be new 3D coordinates of the distal end of the wire. In the example shown in FIG. 10, three-dimensional coordinates can be determined at the time $T_1$ and the time $T_2$, and three-dimensional coordinates at the time $T_3$ are to be found next.

In an X-ray fluoroscopy image 166, three intersection points 162a, 162b, 162c are detected in a template 168 as candidate points corresponding to the distal potion of a guide wire 70. Among these intersection points, the candidate intersection point 162c has the shortest distance along a blood vessel center line 152 from the three-dimensional point one time earlier, and the intersection point 162c is therefore finally selected as a candidate point. This selection is possible because the blood vessel center line 152 has been extracted in the CT image.

Figure 11:
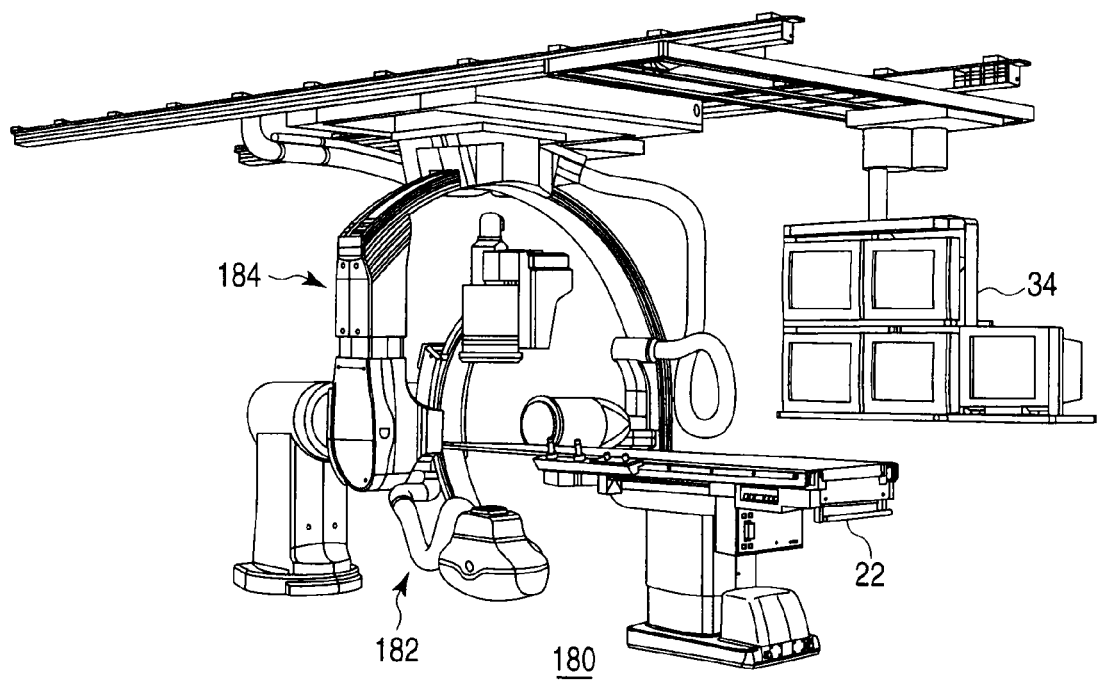
FIG. 11 shows a further modification of one embodiment of the present invention, and is an outside perspective view showing the configuration of a biplane type X-ray diagnostic apparatus.

Furthermore, the embodiment previously described is based on the assumption that the X-ray diagnostic apparatus 20 is a single plane apparatus. However, as the X-ray diagnostic apparatus, a biplane type apparatus capable of simultaneous image pickups in two directions as shown in FIG. 11 may be used. Such a biplane type X-ray diagnostic apparatus 180 comprises a floor mounted C arm device 182 and an overhead traveling Ω arm device 184.

In the X-ray diagnostic apparatus having such a configuration, simple image pickups in two directions make it possible to determine a three-dimensional position X, Y, Z of the wire distal end. Thus, the 3D coordinates of the wire distal end can be more accurately obtained by adding a restrictive condition that the wire distal end is present on the CT 3D blood vessel center line.

Furthermore, when a blood vessel is bent and there are two or more intersection point candidates as described above, a unique intersection point can be obtained if the biplane type X-ray diagnostic apparatus is used.

In addition, the cardiac coronary artery has been described above in the present embodiment, though this is not a restriction, and the present invention is applicable not only to blood vessels of other moving organs but also to blood vessels of static organs. Moreover, the present invention is also applicable to hollow organs such as an esophagus, as well as a blood vessel.

While the embodiment of the present invention has been described above, the present invention is not limited to the embodiment described above, and various modifications can be made without departing from the spirit of the present invention.

Furthermore, the embodiment described above includes inventions at various stages, and suitable combinations of a plurality of disclosed constitutional requirements permit various inventions to be extracted. For example, when the problems described in the section BACKGROUND OF THE INVENTION can be solved and the advantages described in the section BRIEF SUMMARY OF THE INVENTION can be obtained even if some of all the constitutional requirements shown in the embodiment are eliminated, a configuration in which those constitutional requirements are eliminated can also be extracted as an invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
   a first memory configured to store a desired volume three-dimensional image;
   a second memory configured to store a sequentially updated two-dimensional image;
   a processor configured to align the three-dimensional image with the two-dimensional image,
   to acquire a position of a device, and
   to calculate the distal end position of the device in the three-dimensional image; and
   a display configured to display the three-dimensional image and a sectional image of the three-dimensional image including the position of the device,
   wherein
   the display further is configured to display, in the three-dimensional image, a mark indicating three-dimensional coordinates of the position of the device;
   a position of the mark in the three-dimensional image is updated per heartbeat; and
   the sectional image is updated per heartbeat.

2. The image processing apparatus according to claim 1, wherein
   the processor is configured to acquire a distal end position of the device.

3. The image processing apparatus according to claim 1, wherein
   the processor is configured to detect the position of the device.

4. The image processing apparatus according to claim 1, further comprising:
   the processor configured to search for a position of the device after a predetermined time.

5. The image processing apparatus according to claim 1, wherein
   the the processor is configured to calculate an intersection point of a projector and the center line of the three-dimensional image.

6. The image processing apparatus according to claim 5, further comprising:
   the processor configured to select a frame in a predetermined cardiac phase from the two-dimensional image, and to carry out the alignment using the frame selected.

7. An X-ray diagnostic apparatus which displays an image by image processing of image data generated by detecting X-rays applied to a specimen and converting the X-rays to an electric signal, the X-ray diagnostic apparatus comprising:
   a first memory configured to store a desired volume three-dimensional image;
   a second memory configured to store a sequentially updated X-ray two-dimensional image;
   a processor configured to align the three-dimensional image with the X-ray two-dimensional image,
   to acquire a position of a device, and
   to calculate the distal end position of the device in the three-dimensional image; and
   a display configured to display the three-dimensional image and a sectional image of the three-dimensional image including the position of the device,
   wherein
   the display is further configured to display, in the three-dimensional image, a mark indicating three-dimensional coordinates of the position of the device;
   a position of the mark in the three-dimensional image is updated per heartbeat; and
   the sectional image is updated per heartbeat.

8. The X-ray diagnostic apparatus according to claim 7, wherein
   the processor is configured to acquire a distal end position of the device.

9. The X-ray diagnostic apparatus according to claim 7, wherein the processor is configured to detect the position of the device.

10. The X-ray diagnostic apparatus according to claim 7, further comprising:
the processor configure to search for a position of the device after a predetermined time.

11. The X-ray diagnostic apparatus according to claim 7, wherein
the processor configure to calculate an intersection point of a projector and the center line of the three-dimensional image.

12. The X-ray diagnostic apparatus according to claim 11, further comprising:
the processor configured to select a frame in a predetermined cardiac phase from the two-dimensional image, and to carry out the alignment using the frame selected.

* * * * *